United States Patent [19]

Heck

[11] Patent Number: 4,930,355

[45] Date of Patent: Jun. 5, 1990

[54] HYDRAULIC DRIVE APPARATUS AND METHOD FOR INSTRUMENTED PENETRATION AND TENSILE-IMPACT TESTING

[75] Inventor: Siegfried Heck, Sindelfingen, Fed. Rep. of Germany

[73] Assignee: Roboflex Ltd., Switzerland

[21] Appl. No.: 305,895

[22] Filed: Jan. 30, 1989

[30] Foreign Application Priority Data

Jan. 28, 1988 [DE] Fed. Rep. of Germany ....... 3802500

[51] Int. Cl.$^5$ .............................................. G01N 3/00
[52] U.S. Cl. ......................................... 73/840; 73/837
[58] Field of Search .................... 73/12, 838, 840, 837; 92/85 B, 143

[56] References Cited

U.S. PATENT DOCUMENTS

| | | | |
|---|---|---|---|
| 3,631,760 | 1/1972 | Moran | 92/143 |
| 3,973,468 | 8/1976 | Russel, Jr. | 92/85 B |
| 4,611,634 | 9/1986 | Kruckewitt et al. | 92/85 B |
| 4,761,118 | 8/1988 | Zanarini | 92/85 B |

FOREIGN PATENT DOCUMENTS 610736  3/1935  Fed. Rep. of Germany ...... 92/85 B
397794  2/1974  U.S.S.R. .................................... 73/12
777542  11/1980  U.S.S.R. .................................. 73/840
19966  of 1906  United Kingdom .................. 73/840

*Primary Examiner*—Robert R. Raevis
*Attorney, Agent, or Firm*—Lowe, Price, LeBlanc, Becker & Shur

[57] ABSTRACT

Apparatus and a method are provided for tensile-impact and penetration testing of sample elements, utilizing hydraulic flows to accelerate a lead-in piston inside a cylindrical hydraulic chamber in controlled manner to thereby deliver a predetermined amount of energy to a lighter piston mounted on a slidable piston rod to convey the desired force to the sample with minimal distortion of the measured parameters of interest on account of any extraneous oscillations caused by recoil of the elements. The penetration testing is performed preferably by mounting a sample element in a bell-shaped sample-holding element that is easily mounted to an end of the piston rod. A number of penetration sample elements, each held in an individual sample-holding element, can be brought to a selected predetermined temperature and each is readily mountable to the apparatus to enable quick, convenient and inexpensive, reproducible testing of a plurality of samples.

31 Claims, 2 Drawing Sheets

HYDRAULIC DRIVE APPARATUS AND METHOD FOR INSTRUMENTED PENETRATION AND TENSILE-IMPACT TESTING

FIELD OF THE INVENTION

This invention relates to a method for performing penetration testing of sample elements, and, more particularly, to a method of testing such samples by hydraulic means.

BACKGROUND OF THE PRIOR ART

Using plastics, especially enameled plastics body-parts in automobiles, requires testing them for impact-strength at temperatures between +23° and −30° C. As a rule the testing typically involves a tensile-impact test, e.g., per DIN 53,488, by means of pendulum impactors or hydraulic universal testers, and a penetration test carried out with dropping-bolt testers or the already cited universal tester according to DIN, for example, 53,443. Well-grounded conclusions on the suitability of plastics as automobile body parts are reached with present-day knowledge only by resorting to such instrumented test procedures.

In such an instrumented test procedure, applied to the tensile-impact test per DIN 53,448 and to the penetration test per DIN 53,443, the force generated during sample deformation is measured by electronic force pickups and the output is provided as a force-displacement diagram. This diagram allows determination of the work done on the sample and, thereby, the impact strength thereof. This presumes that the force shown in the diagram corresponds to the force acting on the sample and is free of any superpositions from recoil or oscillatory phenomena that would hamper and perhaps make impossible the needed analysis.

The only practical testers presently available are hydraulic universal testers because they alone allow testing over a comparatively wide range of speeds at constant testing rates. However, as discussed further below, they also have drawbacks.

Any tester wherein a mass is being accelerated, such as a pendulum impact tester or a dropping-bolt tester, entails a narrow range of speeds for its applicability. Technical grounds preclude speeds exceeding 5.5 m/s, while the available kinetic energy will usually be too low at speeds less than 2.5 m/s to destroy the sample. At the very least, the speed drops strongly during sample deformation, hence spuriousness is contained in the result.

German patent No. 35 29 470 describes a new tensile-impact tester which is well suited for such tests. This tester, however, does not permit penetration testing. European patent document No. 0079979 B1 describes a hydraulic loading unit, in particular for catapult-systems.

The operational axis of hydraulic testers, as a rule, is vertical and these testers are used for tensile-impact tests in which a sample is connected by a clamping head at its upper end to a force pickup mounted to an upper crossbeam of the tester. The lower sample end is connected by another clamping means to a drive means loosely entering a sleeve fastened to the upper piston rod connected to a piston in a hydraulic cylinder. Such hydraulic cylinders are designed conventionally with piston rods on both sides. The sleeve forms a lead-in path required by the relatively heavy piston for its acceleration to the pre-set speed. The upper end of the sleeve moves along the drive means and thereby ruptures the sample. The force pickup measures the force function while a displacement pickup at the lower piston rod measures the displacement.

In penetration tests with universal testers, a clamping means is mounted to the upper end of the piston rod wherein the pane-shaped sample is fastened. The penetration unit is then mounted to the upper crossbeam, where this unit under DIN 53,443 forms a 20-mm diameter bolt of which a hemispherical end faces the sample. According to said standard, the force sensor in the penetration unit shall be mounted as close as possible to the hemispherical end. The sample and the penetration unit must be apart by such a distance that the piston with the clamping means can be accelerated to the pre-set nominal speed. Designs are furthermore known where the penetration unit is mounted on the piston of the hydraulic cylinder and the clamping means is stationary.

The impinging of the sample on the penetration unit entails the drawback of the sample impacting this unit and, as regards the impulsive traction test, the impact of the drive means on the upper sleeve end when the above-described penetration and impact-strength tests are carried out. Recoil-oscillations are initiated thereby, which are superposed on the force signal, and these aspects hamper and even render impossible its analysis.

The impact-strength tester of the German patent No. 35 29 470 avoids this problem because, according to its teaching, a very lightweight operational piston is connected directly to the sample, and thus recoil-free signals are achieved.

Manufacturers of motor vehicles, plastics and enamels and plastics processors are in need of a testing system allowing the testing of plastics, whether enameled or not, for impact strength, in comparative and reproducible manner, at temperatures between +213° and −30° C. Because the last two cited enterprises frequently are of medium-size, costly testing disproportionate to earnings is ruled out. While such testing nevertheless is necessary, it is important for the economy as a whole to create a testing system which is economical both as regards purchase and operation.

The above-described known universal testers are well beyond the means of such medium-size enterprises both as regards purchase costs and the high requirements of personnel. Moreover the unsatisfactory signal-quality from such apparatus compounds the difficulty. The tensile-impact tester of the German patent No. 35 29 470 can be applied only in a restricted manner, being useful only for tensile-impact tests.

SUMMARY OF THE INVENTION

The principal object of the invention is to create a testing system, suitable for use by means of minor modifications both for penetration and tensile-impact testing, that is less expensive to purchase than the described known testers, of which the operation can be handled by testing technicians or lab assistants, and which offers comparable and reproducible signals from different test points and free of recoil-related errors.

A related object of the invention is to provide a method for performing tests for tensile-impact testing and, with minor modifications, for performing penetration testing on test samples.

These and other objects of the present invention are realized by providing a hydraulic drive apparatus for instrumented tensile-impact testing of a sample element that includes a cylindrical chamber filled with a hydraulic oil and having closed first and second ends provided with central apertures therein and first and second ports adjacent these ends to enable selective inflow or outflow of hydraulic oil therethrough, a lead-in piston contained in the cylindrical chamber to be slidable therein between the ends under the influence of selective hydraulic oil flows through the ports at a speed and direction of motion controlled by the oil flows, the lead-in piston being formed with an axial through aperture, an operational piston that is coaxially mounted to a piston rod slidingly supported by the central apertures and passing through the axial through aperture of the lead-in piston, means for controllably providing the desired hydraulic inflow and outflow to generate controlled movement of the lead-in piston with respect to the operational piston, means for attaching one end of the piston rod to a sample element held along the axis of the piston rod with one end and stationary, and means for determining a force exerted by the piston rod on the sample element.

In another aspect of the invention, particularly suitable for instrumented penetration testing of a sample element, there is provided a hydraulic drive apparatus that differs from the tensile-impact testing apparatus described in the preceding paragraph in that for penetration testing there is provided a means for attaching a sample element to that end of the piston rod that is on the same side as the operational piston with respect to the lead-in piston, and means for penetrating the sample element disposed in a predetermined juxtaposition with respect thereto.

In another aspect of this invention, there is provided a method for tensile-impact testing of a sample with the type of apparatus herein described for this purpose, the method comprising the steps of providing a controlled flow of a hydraulic oil to the hydraulic chamber to thereby accelerate the lead-in piston over the predetermined short distance toward the operational piston to deliver a predetermined amount of impact energy thereto with minimum recoil, and generating signals corresponding to a measured load on and a measured deformation related thereto of the sample.

In yet another aspect of this invention, in a method particularly suitable for penetration testing of a sample, the sample is mounted to a distal end of the piston rod with a gentle biasing force holding the sample element against the penetration portion of a penetrating means, providing the controlled flow of hydraulic oil as in the tensile-impact testing method to generate an impact between the accelerated lead-in piston and the operational piston to provide a force between the sample element and the penetration means whereby the sample is penetrated, and generating signals corresponding to a load experienced by the penetration means in the course of said penetration.

DETAILED DESCRIPTION OF THE PREFERRED EMBODIMENTS

As already mentioned, hydraulic universal testers are equipped with a cylinder comprising a piston with a piston-rod extending on each side. This piston is comparatively heavy and therefore requires a fairly long path to be accelerated to its nominal speed. By contrast, in the design of the invention described below, this heavy piston and hence the path of acceleration and the coupling process transmitting the force into the sample are both avoided. A very light piston initially makes contact with the sample before the actual force transmission. This very light piston can be accelerated in a fraction of a millisecond and hence there is no need for a long path of acceleration for the operational piston. A very short path of acceleration is present between the operational piston and a lead-in piston.

Figure 1:
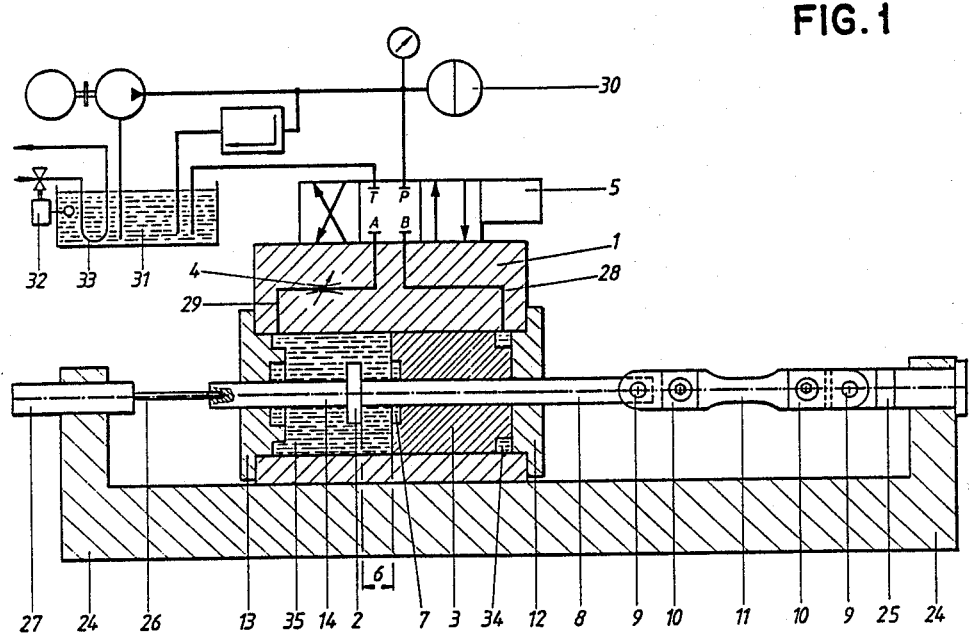
FIG. 1 is a schematic illustration of a preferred embodiment of this invention that is particularly suitable for performing tensile-impact testing on an elongate sample element.

FIG. 1 shows a lead-in piston 3 mounted coaxially with an operational piston 2 inside a cylindrical housing 1. The cross-sectional area of the lead-in piston 3 is larger than the cross-sectional of the operational piston 2. The operational piston 2 is substantially smaller than the housing bore corresponding to the diameter of the lead-in piston 3 and is guided by the front portion 8 of a piston rod in the front housing cover 12 and by the rear portion 14 of the piston rod in the rear housing cover 13. A clamp head 10 is fixed to each side of the sample 11. The clamp heads 10 are linked by plug-in means 9 on one side to the front portion 8 of the piston rod and o the other side to the force pickup 25. The force pickup is mounted on the frame 24. The solenoid plunger 26 of any inductive displacement transducer 27 is mounted on the rear piston rod 14, the transducer being mounted to the frame 24.

The servovalve 5 is mounted in the housing 1. This valve 5 is connected through the conduit 28 to the front space 34 of the housing bore and through the conduit 29 to the rear space 35 of that housing bore. An adjustable throttle 4 is present in the conduit 29 through which a hydraulic oil displaced by the control piston 3 will drain during the testing procedure.

When testing starts, the servovalve 5 sets-up the communication between P and B on one hand and between A and T on the other. The oil moving from the reservoir 30 into the space 34 displaces the lead-in piston 3 towards the operational piston 2, the lead-in piston thereby being accelerated until it has reached a preset speed determined by the adjustment of the throttle 4. Thereupon, provided that the minimal friction is neglected, equal pressure prevails on both sides of the lead-in piston.

The lead-in piston 3 is equipped at its side facing the operational piston 2 with a pressure chamber 7 into which the operational piston 2 fits with minimal play. When the lead-in piston 3 arrives at the operational piston 2, this operational piston blocks the pressure chamber 7 in which thereupon an oil cushion is formed. Then the operational piston 2 is floating on said oil cushion and is carried along by the lead-in piston 3. Thereby the sample 11 is elongated and torn apart. While the lead-in piston 3 moves through the path of acceleration 6, the displaced oil must flow around the operational piston 2. As a result dynamic pressure is generated on the operational piston 2 and produces a slight biasing force pre-stressing without play the plug-in links 9, the sample 11 and the force pickup 25. This biasing force together with the damping of the oil cushion of the pressure chamber 7 when the operational piston 2 is carried along eliminates recoil oscillations at the onset of sample-loading and, therefore, a recoil-free signal reflecting the force-function at the sample is obtained.

Because the operational piston 2 together with the piston rods 8, 14 and the clamping head 10 are held very loosely, they are accelerated within a fraction of a millisecond, the operational piston 2 dipping only minutely into the pressure chamber 7 until its speed matches that of the advance piston. A slight amount of oil passing through the gap between the operational piston 2 and the pressure chamber 7, further through the gap between the advance piston 3 and the piston rod 8, acts as a damper. The pressure prevailing in the pressure chamber and acting on the operational piston is within the conventional range of values of servo-hydraulic testers.

The force being applied from the lead-in piston 3 to accelerate the operational piston 2 and to deform the sample 11 decelerates the lead-in piston. The pressure gradient between the reservoir 30 and the space 34, i.e., the pressure on the front side of the lead-in piston 3 increases. At the same time, the pressure gradient drops between the space 35 and the throttle 4 toward the reservoir 31, i.e., the pressure drops at the side of the lead-in piston facing the operational piston 2. It is known that in hydraulic systems comprising diaphragm-like apertures the pressure required to overcome the flow impedances in the system is proportional to the square of the flow speed. Therefore a slight decrease of the speed of lead-in piston 3 and therefore a slight decrease of the oil flow rate in the system, suffices to produce a pressure difference at the lead-in piston 3 that is enough to accelerate the operational piston and to elongate the sample to rupture. In practice, the decrease in the advance-piston speed is less than the tolerance of the testing speed.

The system is self-regulating due to the large cross-sectional surface of the lead-in piston 3 and the throttle 4 in the drain, accounting for the major part of the pressure difference building up and decaying at the lead-in piston. After the testing system of the invention has been turned ON, the operating personnel need merely preselect the speed by adjustment of the throttle 4 and wait until the hydraulic oil is at a temperature which is kept constant by the cooling-water valve 32 and the radiator 33. Then the testing may begin.

If the hydraulic drive thus described is to be used for penetration tests, the essential components, and thereby the self-regulation as described above, remain the same. The additional or modified components that are otherwise needed are described below. Also described is a penetration test. Identical components with the same functions are denoted by the same numerals in FIGS. 1-4.

Figure 2:
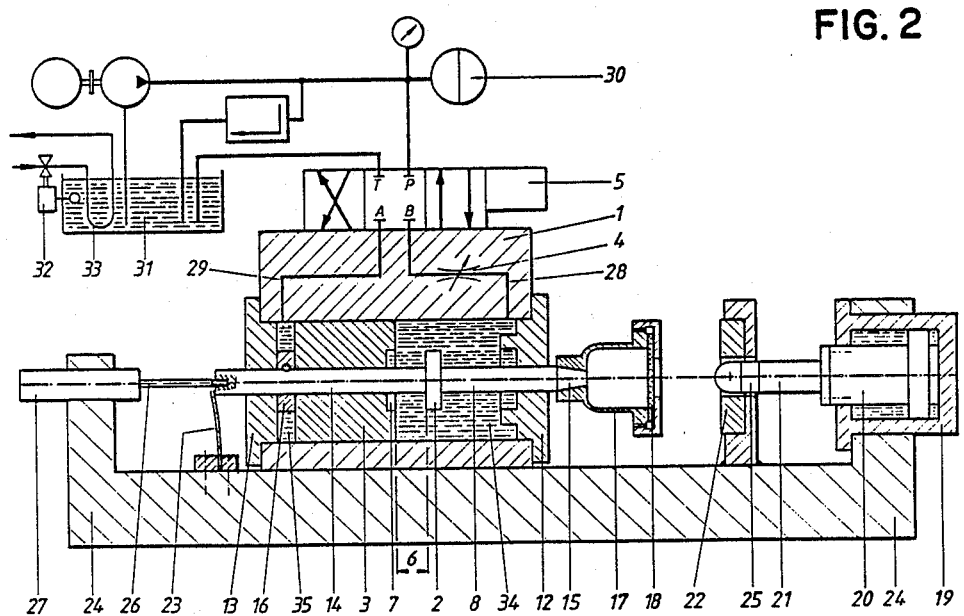
FIG. 2 is a preferred embodiment of the apparatus according to the present invention that is particularly suitable for penetration testing of a sample element.

When the device is used for penetration tests, the front portion 8 of the piston rod is equipped at its distal end with a steep taper 15 receiving a clamping bell 17 with the sample 18 held therein, a disk 16 being mounted on the rear portion of piston rod 14 (best seen in FIG. 2). In this set-up, the operational piston 2 is mounted between the front housing cover 12 and the lead-in piston 3 and the throttle 4 is present in the conduit 28. A matching cylinder 19 is mounted to the frame 24 in such a manner that its axis is aligned with that of the operational piston 2, i.e., coaxially therewith. A penetration unit 21 is mounted to its own piston rod 20. A force pickup 25 is mounted behind the hemispherical tip of the penetration unit and meets predetermined requirements, e.g., of DIN 53,443. A stripper 22 is located between the matching cylinder 19 and the housing 1. In the rest position of the apparatus per FIG. 2, the ports P and A in the servovalve 5 are respectively connected to B and T, and the lead-in piston 3 forces the disk 16 against the rear housing cover 13 and the end of the rear piston rod 14 against a spring 23.

The axis of the described apparatus during its use as a penetration tester is typically oriented to be vertical, hence it is possible to merely set the clamping bell 17 on the taper 15, at the end of front piston rod 8. In the absence of further fastening means, the taper preferably is not self-mounting. The clamping bell 17 therefore can be inserted into the tester merely by manual action, and can be removed from it in the same way. This is significant for temperature-control of the oil in the apparatus. Several clamping bells are used, and into them will be clamped the disk-shaped penetration sample 18. This action takes place outside the tester.

The clamping bells are raised to the required temperature in a separate temperature-control chamber.

Once the clamping bell and the sample are at that temperature, the bell and the sample are removed together from the temperature-control chamber and are set on the taper 15 of the piston rod 8, and the sample is thereafter punched through. At most, 5 seconds will elapse between removal from the temperature-control chamber and sample penetration. The sample is thus reliably and adequately screened by the bell against cooling due to the lower room temperature and retains its selected temperature until penetration occurs. This provision of the invention, that the sample 18 be located within a clamping bell 17 that is easily placed on the piston rod 8 represents an essential advantage over other designs where the clamping bell is rigidly joined to the piston rod of the testing cylinder and where the sample must be individually temperature-controlled in an expensive temperature-control chamber integrated into the tester apparatus. In the present invention, by contrast, a number of thermally-controlled clamping bells with their samples may be kept in a simple temperature-control chamber and the time that is needed for testing is now determined only by the need for recording the test data, and no longer by the time needed to temperature-control the sample.

The simple and economical design of the tester, its low-cost temperature-control, simple operation and quick testing procedure as a whole result in low testing costs which are therefore affordable by medium-size user enterprises.

Figure 3:
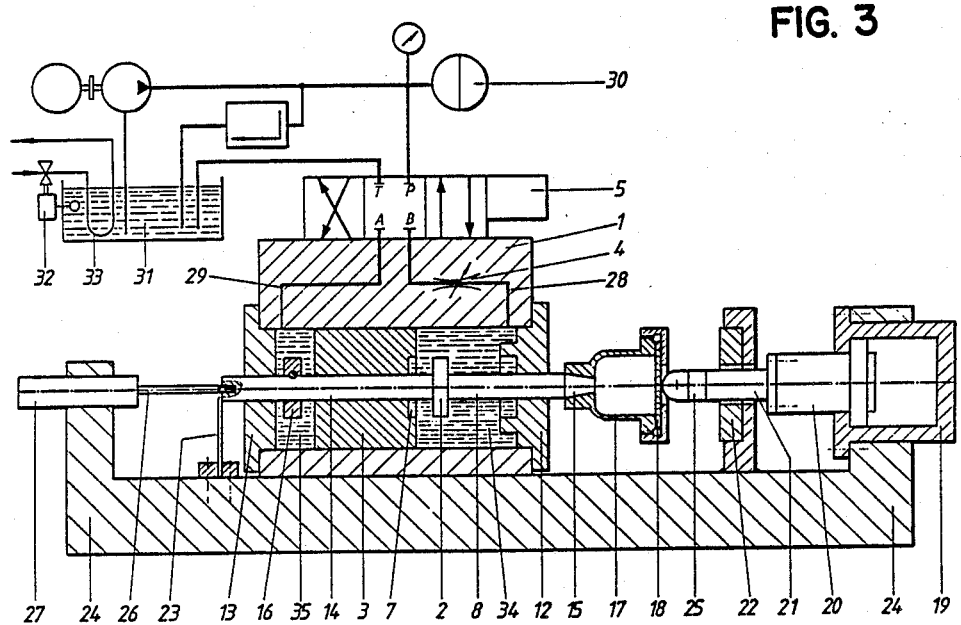
FIG. 3 illustrates the apparatus of FIG. 2 at a time immediately prior to penetration of a test sample.
Figure 4:
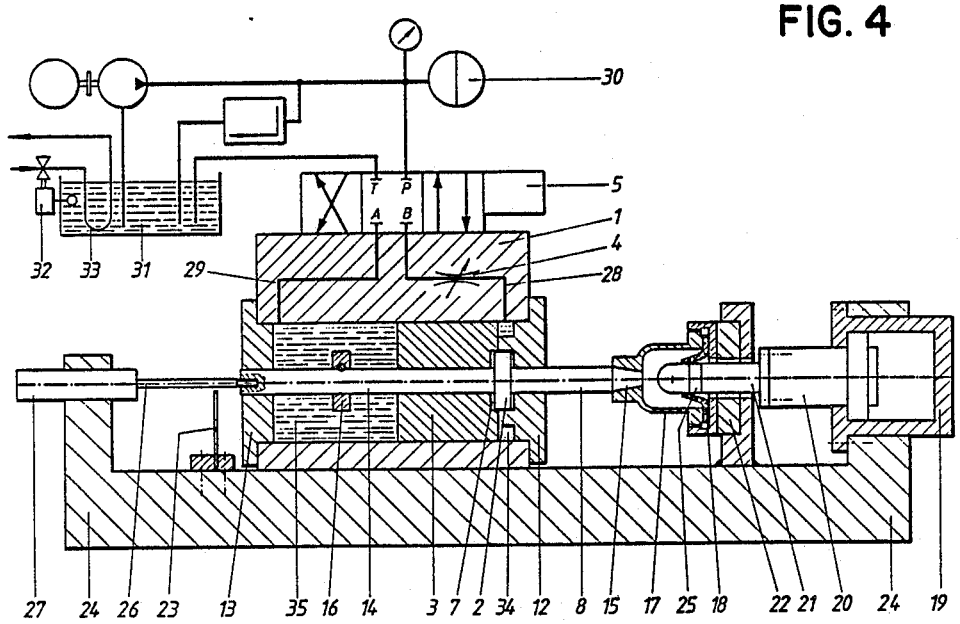
FIG. 4 is the apparatus of FIGS. 2 and 3 following penetration of the sample by the penetration means.

A penetration test according to this invention takes place as follows. A clamping bell 17 fitted with a sample 18 is placed on the taper 15 of the piston rod 8, whereupon the test proper is started. The piston rod 20 of the matching cylinder 19 is advanced until the tip of the penetration unit 21 is about 1-2 mm away from the surface of the sample 18, as best understood with reference to FIG. 3. Ports P and B in the servovalve 5 are then connected to the ports A and T respectively. The lead-in piston 3 thus displaced toward the operational piston 2 and the disk 16 is released. The spring 23 and the pressure of the hydraulic oil flow acting on the operational piston 2 then press by means of the piston rods 14, 8 both the clamping bell 17 and the sample 18 gently but without play against the hemispherical end of the penetration unit 21 (FIG. 3). After the lead-in piston 3 has moved through the path of acceleration 6, it has reached the speed preset by a selected setting of throttle 4 and, by means of the oil cushion in the pressure chamber 7, moves the operational piston 2. The operational sequence and the self-regulation as previously described also relate to the described tensile-impact test in obvious manner. Once the advance piston 3 arrives at the operational piston 2, the very gently held operational piston 2 together with the piston rods portions 8, 14, and the equally very gently held clamping bell 17 with the sample 18 are accelerated within a fraction of a millisecond to the same speed as the lead-in piston 3, and thereby the sample is penetrated. The clamping bell with the sample is penetrated by the penetration unit until the bell impacts the stripper 22, as best understood with reference to FIG. 4. The stripper 22 is preferably made of an elastic material. The distance traveled in the process by the clamping bell is measured by a displacement pickup 27. The matching cylinder 19 then retracts the penetration unit 21 and any elastic sample adhering to the penetration unit is stripped thereby by stripper 22. Lastly, the servovalve 5 reverses and the lead-in piston 3 by means of the disk 16 moves the operational piston 2 together with the piston rods 14, 8 and the clamping bell 17 back into their respective initial positions, as best understood with reference to FIG. 2.

Still other objects and advantages of the present invention will become readily apparent to those skilled in this art from the preceding detailed description, wherein only the preferred embodiments of the invention are illustrated and described, as aforementioned, simply by way of presenting the best modes contemplated of carrying out the invention. As will be realized, the invention is capable of other and different embodiments, and its several details are capable of modifications in various obvious respects, all without departing from the invention. Accordingly, the drawing and description are restrictive, the invention being defined solely by the claims appended hereto.

I claim:

1. Hydraulic drive apparatus, suitable for instrumented impact testing of a sample element, comprising:
   a cylindrical chamber filled with a hydraulic oil, having closed first and second ends provided with central apertures therein and first and second ports adjacent said ends to enable selective inflow or outflow of said hydraulic oil therethrough;
   a lead-in piston having an axial through-aperture contained in said cylindrical chamber so as to be slidable therein between said ends under the influence of said selective hydraulic oil flows through said first and second ports, the speed and direction of motion of said lead-in piston being determined by selected rates and directions of said hydraulic oil flows;
   an operational piston, having a diameter smaller than a diameter of said lead-in piston, coaxially mounted within said chamber to a piston rod that is slidingly supported by said central apertures and slidably passes through said axial through-aperture of said lead-in piston, and disposed between a leading end of said lead-in piston and the adjacent one of said first and second ends of the cylindrical chamber;
   means for controllably providing said selective hydraulic inflow and outflow, to thereby generate controlled movement of said lead-in piston with respect to said operational piston;
   means for transmitting a force from one end of said piston rod to a sample element held stationary to receive said force along the axis of said piston rod; and
   means for determining said force received by said sample element.

2. The hydraulic drive apparatus according to claim 1, wherein:
   said lead-in piston, at an end adjacent said operational piston, has a central recess that is shaped and sized to be able to receive said operational piston therein with a small predetermined clearance therebetween such that motion of said operational piston into said recess of said lead-in piston encounters a predetermined fluid impedance as hydraulic oil is forced out of said recess through said small clearance.

3. The hydraulic drive apparatus according to claim 2, wherein:
   said means for controllably providing said selective hydraulic oil inflow and outflow comprises means for throttling said outflow from said cylindrical chamber.

4. The hydraulic drive apparatus according to claim 2, further comprising:
   means for determining a deformation of said sample under the action of a force exerted thereon by said piston rod.

5. The hydraulic drive apparatus according to claim 2, wherein:
   said force determining means comprises a force responsive transducer attached adjacent an end of said sample element.

6. The hydraulic drive apparatus according to claim 1, wherein:
   said means for controllably providing said selective hydraulic oil inflow and outflow comprises means for throttling said outflow from said cylindrical chamber.

7. The hydraulic drive apparatus according to claim 1, further comprising:
   means for determining a deformation of said sample under the action of a force exerted thereon by said piston rod.

8. The hydraulic drive apparatus according to claim 1, wherein:
   said force determining means comprises a force responsive transducer attached adjacent an end of said sample element.

9. Hydraulic drive apparatus, suitable for instrumented penetration testing of a sample element, comprising:
   a cylindrical chamber filled with a hydraulic oil, having closed first and second ends provided with central apertures therein and first and second ports adjacent said ends to enable selective inflow or outflow of said hydraulic oil therethrough;
   a lead-in piston having an axial through-aperture contained in said cylindrical chamber so as to be slidable therein between said ends under the influence of said selective hydraulic oil flows through said first and second ports, the speed and direction of motion of said lead-in piston being determined by selected rates and directions of said hydraulic oil flows;
   an operational piston, having a diameter smaller than a diameter of said lead-in piston, coaxially mounted to a piston rod that is slidingly supported by said central apertures and slidably passes through said axial through-aperture of said lead-in piston, and disposed between a leading end of said lead-in piston and the adjacent one of said first and second ends of the cylindrical chamber;

means for attaching a sample element to that end of the piston rod that is on the same side as said operational piston with respect to said lead-in piston; and means for penetrating said sample element, disposed in a predetermined juxtaposition with respect to said sample element.

10. The hydraulic drive apparatus according to claim 9, wherein:
that end of said piston rod to which said attaching means is attached is formed to have a predetermined taper, and said attaching means is formed to have a corresponding tapered aperture for fitting to said taper formed on said piston rod in readily detachable manner.

11. The hydraulic drive apparatus according to claim 9, wherein:
said attaching means comprises a bell-shaped element having an open end formed to hold said sample element therein in position for penetration by said means for penetrating in correspondence with a predetermined movement of said piston rod.

12. The hydraulic drive apparatus according to claim 9, further comprising:
a spring disposed to bias said piston rod and said sample element mounted thereon lightly against said penetrating means prior to penetration of said sample thereby.

13. The hydraulic drive apparatus according to claim 9, wherein:
said penetrating means comprises a penetrating element of predetermined shape and size mounted to a piston slidably contained within a hydraulic cylinder.

14. The hydraulic drive apparatus according to claim 9, further comprising:
temperature control means for ensuring that said sample element attaching means and said sample element attached thereto are both at a selected predetermined temperature when said penetration is performed.

15. The hydraulic drive apparatus according to claim 9, further comprising:
means for controlling a temperature of said hydraulic oil.

16. The hydraulic drive apparatus according to claim 9, wherein:
said lead-in piston, at an end adjacent said operational piston, has a central recess that is shaped and sized to be able to receive said operational piston therein with a small predetermined clearance therebetween such that motion of said operational piston into said recess of said lead-in piston encounters a predetermined fluid impedance as hydraulic oil is forced out of said recess through said small clearance.

17. The hydraulic drive apparatus according to claim 16, wherein:
that end of said piston rod to which said attaching means is attached is formed to have a predetermined taper, and said attaching means is formed to have a corresponding tapered aperture for fitting to said taper formed on said piston rod in readily detachable manner.

18. The hydraulic drive apparatus according to claim 16, wherein:
said attaching means comprises a bell-shaped element having an open end formed to hold said sample element therein in position for penetration by said means for penetrating in correspondence with a predetermined movement of said piston rod.

19. The hydraulic drive apparatus according to claim 16, further comprising:
a spring disposed to bias said piston rod and said sample element mounted thereon lightly against said penetrating means prior to penetration of said sample thereby.

20. The hydraulic drive apparatus according to claim 16, wherein:
said penetrating means comprises a penetrating element of predetermined shape and size mounted to a piston slidably contained within a hydraulic cylinder.

21. The hydraulic drive apparatus according to claim 16, further comprising:
temperature control means for ensuring that said sample element attaching means and said sample element attached thereto are both at a selected predetermined temperature when said penetration is performed.

22. The hydraulic drive apparatus according to claim 16, further comprising:
means for controlling a temperature of said hydraulic oil.

23. A method for performing a load test on a sample element that is mounted stationarily to receive a force from a piston rod movable by a force conveyed thereto by a light operational piston mounted coaxially thereon when the operational piston experiences a force by an impact therewith by a hydraulically driven heavier lead-in piston that has a diameter larger than a diameter of the operational piston and is disposed to controllably slide coaxially with respect to the operational piston and the piston rod in a hydraulic chamber, comprising the steps of:
providing a controlled flow of a hydraulic oil to said hydraulic chamber, to thereby accelerate said lead-in piston over a predetermined short distance toward said operational piston to deliver a predetermined amount of energy upon impact therewith with minimal recoil; and determining an actual load experienced by said sample element and a related deformation thereof.

24. The method according to claim 23, comprising the further step of:
generating output signals corresponding to said measured load and deformation.

25. The method according to claim 23, including the further step of:
providing a recess in an end of said lead-in piston adjacent said operational piston, of size and shape such as to permit reception of said operational piston within said recess with a predetermined small clearance, thereby providing a predetermined fluid impedance to said reception in order to minimize oscillatory distortions of said output signals.

26. The method according to claim 23, comprising the further step:
controlling a temperature of hydraulic oil in said hydraulic chamber.

27. A method for performing a penetration test on a sample element by penetration thereof by relative motion between the sample element and a stationary penetration means by force provided to said sample element by a piston rod movable by force transmitted thereto by a light operational piston mounted coaxially thereon when the operational piston experiences a force by an impact therewith by a hydraulically driven heavier lead-in piston that has a diameter larger than a diameter of the operational piston and is disposed to slide coaxially with respect to the operational piston and the piston rod in a hydraulic chamber, comprising the steps of:

mounting a sample element to an end of the piston rod such that the sample element is in a predetermined juxtaposition with respect to a penetrating portion of the penetration means;

providing a controlled flow of a hydraulic oil to said hydraulic chamber to thereby accelerate said lead-in piston over a predetermined short distance toward said operational piston to deliver a predetermined amount of energy by impact therewith with minimum recoil; and generating signals corresponding to a load experienced by said penetration means as the same penetrates said sample moved relative thereto.

28. The method according to claim 27, comprising the further step of:

applying an initial biasing force to said sample element to lightly bias the same against said penetration portion of said penetration means prior to application of said force thereto.

29. The method according to claim 27, comprising the further step of:

controlling a temperature of said sample element to a selected predetermined value immediately prior to mounting said sample element for the application of said force thereto.

30. The method according to claim 27, comprising the further step of:

controlling a temperature of the hydraulic oil used to accelerate said lead-in piston toward said operational piston.

31. The method according to claim 27, comprising the further step of:

stripping said penetrated sample element form said penetration means following said penetration.

* * * * *